United States Patent [19]

Kurtz

[11] E Re. 29,909

[45] Reissued Feb. 13, 1979

[54] METHOD OF CLEANSING CONTAMINATED WOUNDS

[75] Inventor: Leonard D. Kurtz, Woodmere, N.Y.

[73] Assignee: Deknatel Inc., Long Island, N.Y.

[21] Appl. No.: 821,963

[22] Filed: Aug. 4, 1977

Related U.S. Patent Documents

Reissue of:

[64] Patent No.: 3,997,458
Issued: Dec. 14, 1976
Appl. No.: 460,451
Filed: Apr. 12, 1974

[51] Int. Cl.[2] ..... C11D 1/72; C11D 3/48

[52] U.S. Cl. ..... 252/89 R; 252/106; 424/80; 424/150; 424/78

[58] Field of Search ..... 252/89, 106; 424/78, 424/80, 150

[56] References Cited

U.S. PATENT DOCUMENTS

| | | | |
|---|---|---|---|
| 2,739,922 | 3/1956 | Shelanski | 424/150 X |
| 3,326,806 | 6/1967 | Dolby | 252/106 |
| 3,367,877 | 2/1968 | Cantor et al. | 252/106 |
| 3,539,520 | 11/1970 | Cantor et al. | 252/106 |
| 3,728,449 | 4/1973 | Cantor et al. | 424/150 |
| 3,730,960 | 5/1973 | Watchung et al. | 424/78 |
| 3,855,140 | 12/1974 | Billany et al. | 252/106 |

FOREIGN PATENT DOCUMENTS 526585 3/1954 Belgium.

*Primary Examiner*—P.E. Willis, Jr.
*Attorney, Agent, or Firm*—Larson, Taylor and Hinds

[57] ABSTRACT

Aqueous detergent solutions of block copolymers of ethylene oxide and propylene oxide having the structure:

$$HO(C_2H_4O)_a(\underset{\underset{CH_3}{|}}{CH}-CH_2O)_b(C_2H_4O)_cH$$

and an ethylene oxide to propylene oxide ratio of at least 4:1 have been found to be surprisingly useful in the cleansing of contaminated wounds in that they do not impair the wound's ability to resist infection. Surgical scrub solutions of these detergent solutions containing in addition antiseptic agents provide cleansing solutions which both eliminate bacteria and provide the desired cleansing action without impairing the wound's ability to resist infection.

8 Claims, No Drawings

METHOD OF CLEANSING CONTAMINATED WOUNDS

Matter enclosed in heavy brackets [ ] appears in the original patent but forms no part of this reissue specification; matter printed in italics indicates the additions made by reissue.

FIELD OF THE INVENTION

This invention relates to the cleansing of contaminated wounds. More particularly the invention is directed to use of certain nonionic surfactant solutions in the cleansing of wounds.

BACKGROUND OF THE INVENTION

Recommendations for immediate care of the soft tissue injuries include cleaning the area surrounding the wound and the wound itself. Practices vary somewhat in the selection of and use of the cleansing agent for cleansing the skin and the wound. The use of detergents of surfactants for wound cleaning, outside of a very few exceptions are ordinarily avoided because of their harmful effects on wound healing. In other words, despite the fact that many detergents are highly effective cleaning agents and do an excellent job in removing foreign substances from a wound they are nevertheless "toxic" in the sense that they impair the wound's tissue's ability to resist infection. Of special note is the fact that other standards or measurements of toxicity, for instance, oral toxicity, intravenous toxicity and skin sensitivity have not been found to bear a direct relationship to the ability of a detergent to impair a wound's ability to resist infection. A number of detergents acknowledged or classed as non-toxic on the basis of other studies unfortunately prove toxic to wound healing, that is, do in fact impair the wound's ability to resist infection.

Among the commercially available surgical scrub solutions which have been used by surgeons are pHisoHex and Betadine. The harmful effects of even these solutions have been reported and confirmed by studies in Custer, J., Edlich, R. F., Prusak, M. Madden, J., Panek and Wangensteen, O. H. "Studies in the management of the contaminated wound V. An assessment of the effectiveness of pHisoHex and Betadine surgical scrub solutions." Amer. J. Surg. 121:572, 1971. These surgical scrub solutions are mixtures of an antiseptic agent and a surface active detergent, the antiseptic agent being employed to destroy the viable bacteria in the wound while the surface active agent is utilized as a cleansing agent to remove foreign bodies from the wound surface. It was found that treatment of the contaminated wounds in guinea pigs with either of these surgical scrub solutions increased the wound's susceptibility to bacterial infection. In fact, the incidence of infection after treatment of the contaminated wounds with these surgical scrub solutions was higher than the infection rate of wounds subjected to 0.9% sodium chloride solution. The antiseptic agents in the surgical solutions while exerting a favorable influence on contaminated wounds fails to eliminate the harmful effect of the detergents.

As a consequence of the increasing evidence on the harmful effects of detergents on wounds, most surgeons today simply irrigate the wound with large amounts of 0.9% sodium chloride solution.

Needless to say a need exists in the cleaning of contaminated wounds for a cleaning agent which possesses the desired effective cleansing action without the adverse effects on wound healing that characterize prior art detergent-containing surgical scrubs. It is one object of the invention, therefore, to satisfy this need. Another object of the invention is to provide a new detergent-containing surgical scrub solution which provides antiseptic benefits without impairment to wound healing.

SUMMARY OF THE INVENTION

This and other objects of the invention are obtained by selecting, as the cleansing solution in the cleansing of contaminated wounds, an aqueous detergent solution containing as the detergent a block copolymer of ethylene oxide and propylene oxide having the structure:

$$HO(C_2H_4O)_a(\underset{\underset{CH_3}{|}}{CH}-CH_2O)_b(C_2H_4O)_cH$$

where b is below about 25% and $(C_2H_4O)_{a+c}$ is at least 75%, preferably up to 95% of the total weight of the copolymer, said copolymer having an average molecular weight of about 5,000 to 15,500. The preferred block copolymers of the invention have a molecular weight of about 5,000 to 13,500 and a $(C_2H_4O)_{a+c}$, i.e. an ethylene oxide content of at least 75% *(i.e. a ratio of at least 3:1)*. It is important to note that while the molecular weight of the copolymers has not been found to be a particularly important determinant of the toxicity of the detergents in body wounds, the content of ethylene oxide is critical and an important causal factor of toxicity. It has been surprisingly discovered that if a copolymer having an ethylene oxide content of at least 75% is selected as the surfactant in cleansing of contaminated wounds there is no impairment of the wound's natural resistance to infection. This is in sharp contrast to the results obtained with solutions of copolymers having less than 75% ethylene oxide content where high incidences of infection in wounds receiving these copolymers is encountered.

In another embodiment of the invention a novel surgical scrub solution is obtained comprising an aqueous detergent solution containing as a surfactant the above described block copolymer and an antiseptic.

DETAILED DESCRIPTION OF THE INVENTION

The block copolymers of the invention are commercially available members of a family comprised of an almost unlimited number of nonionic surfactants commonly referred to as Pluronic Polyols. The pluronic Polyols are a series of block copolymers that consist of water-soluble poly(oxyethylene) groups at both ends of a water-insoluble poly(oxypropylene) chain. The first step in making the surfactants of the present invention is the controlled addition of propylene oxide to the two hydroxyl groups of a propylene glycol nucleus. The resulting polyoxypropylene glycol becomes water-insoluble at a molecular weight of 900. The hydrophobe is then tailored to the desired molecular weight and ethylene oxide added to sandwich the hydrophobic base between hydrophilic poly(oxyethylene) group which are controlled in length. The surfactants of the present invention is that narrow group in which the ethylene oxide addition is controlled to constitute at least 75% by weight of the final molecule. Illustrative of commercially available Pluronic Polyols suitable for use in the invention are polyol products of BASF Wyandotte Corporation designated F38, F68, F88, F98 and F108. Particularly preferred in Pluronic Polyol F68.

In brief, the surfactants may be prepared employing the following illustrative general procedure:

A stainless steel reaction chamber is first purged with nitrogen and propylene glycol and sodium hydroxide and heated to 120° C with gentle agitation until the sodium hydroxide has dissolved. Propylene oxide is added as fast as it will react, maintaining a temperature of 120° C., until the desired molecular weight is obtained. Then the desired amounts (75% or greater) of ethylene oxide is added at such a rate as to maintain the desired reaction temperature of 120° C. When all the ethylene oxide has been added, the reaction chamber may be stripped of low-boiling olymers. The reaction mixture is then neutralized, usually with phosphoric acid, to a pH of 7 ± 1. The neutral salts are removed mechanically by filtration and the product is cooled.

A more detailed disclosure of the preparation of the surfactants can be found, for instance, in U.S. Pat. No. 2,674,619, hereby incorporated by reference.

The surfactants of the invention are all water-soluble exhibiting a solubility in water of greater than 10 grams per 100 ml. Thus, the cleansing solutions employed in the invention may be prepared by simply dissolving the copolymer in water. The concentration of the copolymer in the water may vary with the only important critera being that it be present in deterge amounts, that is, in sufficient concentrations to detergent or effect cleansing action. In general, concentrations of at least about 10%, usually up to about 25% by weight have been found suitable.

If desired, the cleansing solutions of the present invention may include other materials commonly employed in surgical scrub solutions. For instance, and in accordance with another aspect of the present invention, a novel surgical scrub solution is provided by including in the detergent solution of the invention an antiseptic. The antiseptic can be any of the known antiseptic agents, particularly those conventionally included in surgical scrub solutions. Such antiseptic agents include, for example, ethyl alcohol, benzalkonium chloride, chloramine, iodine, iodophors such as polyvinylpyrrolidoneiodine, and the like. The surfactants of the invention form stable, soluble complexes with elemental iodine as has been described in deHavarre, M. G. and Bailey, H. G. "The interference of nonionic emulsifiers with preservatives. "J. Soc. Cosmet. Chem. 7:427, 1956. The present invention contemplates using aqueous solutions of complexes of the copolymer and iodine as surgical scrub solutions wherein the surfactant copolymer provides the cleansing action and the iodine eliminates the bacterial pathogens. The antiseptic agents in the scrub solutions is employed in effective amounts usually ranging from about 0.5 to 5.0 percent by weight.

Any of the various cleansing or scrubbing techniques known in the art for cleansing of wounds may be employed in the invention such as swabbing or scrubbing with gauze, sponges, surgical cotton and the like moistened with the cleansing solution, simple irrigation of the wound with the solution and the like.

The following examples are included to further illustrate the present invention. In all of the examples the standardized preparation of the animal, the technique of wounding, and the bacterial culture procedure was that reported in Edlich, R. F., Tsung, M. S., Rogers, W., Rogers, P. and Wangensteen, O. H. "Studies in the management of the contaminated wound. I. Technique of closure of such wounds together with a note on a reproducible model." J. Surg. Res. 8:585, 1968. Two standardized incisions, parallel and equidistant from the vertebral column, were made in each guinea pig. Five minutes after wounding, a predetermined number of a strain of Staphylococcus aureus (ATCC No. 12,600) was delivered to the wound. A designated solution (0.1 ml.) was instilled into the wound 5 minutes later. Five minutes after the topical treatment, the edges of the wounds were approximated with microporous tapes. Four days after treatment, the inflammatory responses of the wounds were determined.

In each case the inflammatory responses assessed were the presence of gross infection and wound induration. Induration about the wound was determined by palpating the wound with a gloved finger and measuring the width of the indurated margin of each wound in millimeters. The wound was then opened and inspected for evidence of purulent exudate. For confirmation of the presence of bacteria, a culture was taken by swabbing the wound with a cotton-tipped applicator. The induration measurements were analyzed using Student's test for varied differences. The significance of the gross infection score and positive culture data was determined by the sign test.

EXAMPLE I

The effect of topical application of 1 ml of 10% solutions of Pluronic Polyols of varying molecular weight, with a wide range of ethylene oxide content, on guinea pig wound's resistance to infection was studied. Utilizing standarized wounds contaminated with a designated number of bacteria, the influence of the polyol on the wound's resistance to infection was ascertained by comparing the infection rate of contaminated wounds subjected to one polyol to the incidence of infection in controlled contaminated wounds subjected to another polyol. The wound culture results, the wound induration and the incidence of infection in the treatments are all shown in Table 1 below.

Table 1

Influence of Molecular Weight of Pluronic Polyols on Their Toxicity in Surgical Wounds

| | Inoculum | Pluronic Polyol | | Inflammatory Response | | | | |
|---|---|---|---|---|---|---|---|---|
| | | | | Induration | | Gross Infection | | Culture |
| No. Animals* | (no. bacteria | Molecular Weight | FO:PO Ratio | (mm) | (P) | (% positive) | (P) | (% positive) |
| 9 | $10^6$ | 8,350 | 4:1 | 5.8 ± 1.8 | <0.01 | 11.1 | NS | 100.0 |
| | | 14,000 | 4:1 | 7.0 ± 2.3 | | 33.3 | | 100.0 |
| 18 | $10^7$ | 8,350 | 4:1 | 5.6 ± 1.6 | <0.01 | 61.1 | NS | 100.0 |
| | | 14,000 | 4:1 | 7.1 ± 1.6 | | 83.3 | | |
| 8 | $10^8$ | 8.350 | 4:1 | 9.5 ± 1.8 | NS | 100.0 | NS | 100.0 |
| | | 14,000 | 4:1 | 8.9 ± 1.1 | | 100.0 | | 100.0 |
| 10 | $10^6$ | 5,000 | 4:1 | 5.3 ± 1.8 | <0.05 | 50.0 | NS | 100.0 |

Table 1-continued

Influence of Molecular Weight of Pluronic Polyols on Their Toxicity in Surgical Wounds

| No. Animals* | Inoculum (no. bacteria | Pluronic Polyol Molecular Weight | Pluronic Polyol FO:PO Ratio | Inflammatory Response Induration (mm) | Induration (P) | Gross Infection (% positive) | Gross Infection (P) | Culture (% positive) |
|---|---|---|---|---|---|---|---|---|
| | | 14,000 | 4:1 | 6.3 ± 1.9 | | 66.7 | | 100.0 |
| 12 | $10^7$ | 5,000 | 4:1 | 8.3 ± 1.3 | <0.05 | 90.0 | NS | 100.0 |
| | | 14,000 | 4:1 | 9.6 ± 1.3 | | 100.0 | | 100.0 |
| 11 | $10^5$ | 5,000 | 1:4 | 5.6 ± 1.2 | NS | 72.7 | NS | 100.0 |
| | | 1,630 | 1:4 | 5.6 ± 1.9 | | 72.7 | | 100.0 |

[a]Not significant
*guinea pigs

The results of Table 1 show that the incidence of gross infection in contaminated wounds after the application of a high molecular weight polyol did not differ significantly from the infection rate of wounds treated with a polyol with the same ethylene oxide:propylene oxide ratio (EO:PO ratio) and a lower molecular weight. However, the width of indurated margins of wounds treated with a polyol with a molecular weight of 14,000 was significantly greater than the width of indurated edges of wounds subject to a polyol with the same EO:PO ratio (4:1) and a lower molecular weight 5,000 and 8350). The molecular weight of the Pluronic polyols with low ethylene oxide content had no significant influence on the tissue's inflammatory response. The width of the indurated margins of wounds receiving Pluronic polyols with a 1:4 EO:PO ratio and a wide range of molecular weights did not differ significantly.

EXAMPLE II

Utilizing Pluronic polyols with similar molecular weights, the incidence of infection of wounds treated with polyols containing 80% ethylene oxide (by weight) was compared to Pluronic polyols containing 20% and 50% ethylene oxide (by weight). The results of the comparison are shown in Table 2.

Table 2

Influence of Ethylene Oxide Content of Pluronic Polyols on Their Toxicity in Surgical Wounds

| No. Animals* | Inoculum (no. bacteria) | Pluronic Polyol Molecular Weight | Pluronic Polyol EO:PO Ratio | Inflammatory Response Induration (mm) | Induration (P) | Cross Infection (% positive) | Cross Infection (P) | Culture (% positive) |
|---|---|---|---|---|---|---|---|---|
| 14 | $10^5$ | 5000 | 1:4 | 5.8 ± 2.4 | <0.01 | 71.0 | <0.05 | 100.0 |
| | | 5000 | 4:1 | 4.4 ± 2.5 | | 28.0 | | 100.0 |
| 21 | $10^5$ | 4600 | 1:1 | 5.0 ± 1.0 | <0.01 | 52.4 | <0.05 | 100.0 |
| | | 5000 | 4:1 | 4.3 ± 0.6 | | 14.3 | | 100.0 |

*guinea pigs

The data of Table 2 shows that the incidence of infection of wounds treated with a polyol containing 80% ethylene oxide was significantly lower than the infection rate of the wounds receiving a polyol with an EO:PO ratio of either 1:1 or 1:4. The width of the indurated edges of the wounds receiving a polyol with a 4:1 EO:PO ratio was significantly smaller than the width of the indurated edges of wounds treated with Pluronic polyols containing less ethylene oxide.

EXAMPLE III

The effect of a 10% aqueous solution of a Pluronic polyol (0.1 ml) having a molecular weight of 8,350 and a EO:PO ratio of 4:1 on a wound's resistance to infection was compared with 0.9% sodium chloride solution at different bacteria contamination levels. The results are shown in Table 3 below.

Table 3

Effect of a Pluronic Polyol[a] Exhibiting an 80% Ethylene Oxide Content on the Wound's Resistance to Infection

| No. Animals* | Inoculum (no. bacteria) | Treatment | Inflammatory Response Induration (mm) | Induration (P) | Gross Infection (% positive) | Gross Infection (P) | Culture (% positive) |
|---|---|---|---|---|---|---|---|
| 16 | $10^5$ | Pluronic | 5.3 ± 1.5 | NS[b] | 12.5 | NS | 100.0 |
| | | 0.85% NaCl | 5.7 ± 1.6 | | 25.0 | | 100.0 |
| 25 | $10^6$ | Pluronic | 6.6 ± 2.6 | NS | 20.0 | NS | 100.0 |
| | | 0.85% NaCl | 6.5 ± 2.0 | | 28.0 | | 100.0 |
| 27 | $10^7$ | Pluronic | 6.6 ± 1.7 | NS | 40.8 | NS | 100.0 |
| | | 0.85% NaCl | 7.1 ± 1.8 | | 40.8 | | 100.0 |

[a]Molecular weight 8,350, EO:PO ratio 4:1.
[b]Not significant.
*guinea pigs

The data of Table 3 shows that the incidence of gross infection of wounds treated with the polyols of the invention containing an ethylene oxide content of 80% did not differ significantly from the control wounds subjected to 0.9% sodium chloride.

Pluronic polyols of the present invention having an EO:PO ratio of 4:1 and a molecular weight of 8,350 was added to Betadine antiseptic solution to prepare a surgical scrub solution. Betadine antiseptic solution contains the idophor polyvinylpyrrolidone-iodine. The therapeutic value of the resulting Pluronic polyol-Betadine antiseptic solution mixture was compared with the commercially available Betadine surgical scrub solution in the treatment of contaminated wounds. Betadine surgical scrub solution contains an anionic detergent and the polyvinylpyrrolidone-iodine. The results of the tests are shown in Table 4 below.

Table 4

Therapeutic Value of Surgical Scrub Solutions Containing a Pluronic Polyol in the Treatment of the Contaminated Wound

| No. Animals* | Inoculum (no. bacteria) | Surgical Scrub Solution: Antiseptic solution | Surgical Scrub Solution: Detergent | Inflammatory Response: Induration (mm) | Induration (P) | Gross Infection (% positive) | Gross Infection (P) | Culture (% positive) | Culture (P) |
|---|---|---|---|---|---|---|---|---|---|
| 12 | $10^6$ | PVP-Iodine | Nonionic pluronic[a] | 4.3 ± 0.5 | <0.01 | 0.0 | <0.05 | 50.0 | <0.05 |
| | | PVP-Iodine | Anionic | 7.8 + 2.6 | | 66.6 | | 100.0 | |

[a]4:1 EO:PO ratio and 8,350 MW.
*guinea pigs

The results of Table 4 establish that the therapeutic value of the Pluronic polyol-Betadine antiseptic solution mixture was significantly greater than the commercially available Betadine Surgical Scrub solution in the treatment of contaminated wounds. None of the wounds treated with the polyol-Betadine antiseptic mixture exhibited infection as compared to the 66.6% of the wounds receiving Betadine surgical scrub solution. The efficacy of the polyol-Betadine antiseptic agent scrub was further apparent from the culture data. Staphylococcus areus was recovered from all wounds treated with the betadiene surgical scrub solution. Only 50% of the wounds treated with Pluronic-Betadine antiseptic solution exhibited Staphylococcus aureus. The difference between the incidence of sterile cultures in the two treatment groups is significant at the 0.05 level of confidence.

EXAMPLE IV 72 guinea pigs were anesthetized, shaved, and depilated. Each animal then received two standardized, paravertebral incisions of 3 cm. length down to the panniculus carnosus. After wounding the animals were divided into two large groups and each wound in a specified group received 0.02 ml of inoculum containing either $1.0 \times 10^6$ or $10^7$ bacteria. The bacteria employed were a penicillin sensitive strain of S. aureus (ATCC No. 12,600). Within each large group the animals were further divided into four treatment groups. Wounds in a designated treatment group received 0.1 ml of a 10% solution of either Pluronic polyol F-68, F-98 or F-87, having the molecular weight and percent ethylene oxide set out in the table below. Wounds in the fourth treatment group received 0.1 ml of isotonic saline and served as controls. After the solutions had remained on the wounds for 15 minutes, the wound edges were approximated with microporous tape and the animals were sacrificed and the inflammatory responses of their wounds evaluated. The inflammatory responses assessed were wound induration and the presence of purulent exudate. An estimate of the number of viable bacteria present in each wound was also made.

| Compound | % Ethylene Oxide | Molecular Weight |
|---|---|---|
| F-87 | 70% | 7700 |
| F-68 | 80% | 8000 |
| F-98 | 80% | 13,500 |

The results of the study are shown in Table 5 below.

Table 5

| Inoculum | Treatment | Induration (mm) | Induration (p) | Gross Infection (% pos.) | Gross Infection (p) | Viable Bacteria ($10_6$) | Viable Bacteria (p) |
|---|---|---|---|---|---|---|---|
| $10^6$ | Saline* | 5.2 ± 0.9 | — | 17 | — | 5.43 ± 0.60 | — |
| | F-68 | 5.0 ± 0.9 | NS | 33 | NS** | 5.63 ± 1.14 | NS |
| | F-98 | 6.2 ± 1.3 | NS | 50 | NS | 5.64 ± 0.84 | NS |
| | F-87 | 5.6 ± 0.9 | NS | 67 | 0.05 | 6.00 ± 1.01 | NS |
| $10^7$ | Saline | 10.5 ± 1.9 | — | 100 | — | 6.72 ± 0.29 | — |
| | F-68 | 10.3 ± 1.2 | NS | 100 | NS | 6.83 ± 0.29 | NS |
| | F-98 | 8.9 ± 1.1 | NS | 100 | NS | 6.72 ± 0.29 | NS |
| | F-87 | 11.8 ± 1.6 | NS | 100 | NS | 7.05 ± 0.28 | 0.01 |

*0.9%
**not significant

Table 5 shows that Pluronic polyols containing 70% of ethylene oxide by weight impairs the wound's ability to resist infection. This finding is in sharp contrast with the results encountered in treating the contaminated wounds with Pluronic polyol F-68 and F-98. Contaminated wounds subjected to therapeutic treatment with these pololys had an infection rate which did not differ from the infection rate of contaminated wounds subjected to 0.9% saline.

It is claimed:

1. In the cleansing of contaminated wounds with a surgical scrub solution, the improvement which comprises employing as the surgical scrub solution an aqueous detergent solution which does not impair the wound's ability to resist infection, consisting of an aqueous solution of at least about 10% by weight of a block copolymer of ethylene oxide and propylene oxide having the structure:

$$HO(C_2H_4O)_a(\underset{\underset{CH_3}{|}}{CH}-CH_2O)_b(C_2H_4O)_cH$$

wherein the ratio of $(C_2H_4O)_{a+c}$ to $_b$ is at least about [4:1] *3:1* said copolymer having an average molecular weight of about 5,000 to 15,500.

2. The improvement of claim 1 wherein the molecular weight of the copolymer is about 5,000 to 13,500.

3. The improvement of claim 1 wherein the molecular weight of the copolymer is about 5,000 to 13,500 and $(C_2H_4O)_{a+c}$ is about 80%.

4. The improvement of claim 3 wherein the copolymer has a molecular weight of 8,350.

*5. The improvement of claim 1 wherewith the ratio of $(C_2H_4O)_{a+c}$ to $_b$ is at least about 4:1.*

*6. The improvement of claim 5 wherein the molecular weight of the copolymer is about 5,000 to 13,500.*

*7. The improvement of claim 5 wherein the molecular weight of the copolymer is about 5,000 to 13,500 and $(C_2H_4O)_{a+c}$ is about 80%.*

*8. The improvement of claim 7 wherein the copolymer has a molecular weight of 8,350.*

* * * * *